United States Patent [19]

Shum

[11] Patent Number: 4,950,828

[45] Date of Patent: Aug. 21, 1990

[54] PROCESS FOR UPGRADING LIGHT PARAFFINS

[75] Inventor: Victor K. Shum, Naperville, Ill.

[73] Assignee: Amoco Corporation, Chicago, Ill.

[21] Appl. No.: 375,139

[22] Filed: Jun. 30, 1989

[51] Int. Cl.$^5$ ................................................. C07C 2/52
[52] U.S. Cl. ..................................... 585/417; 585/419
[58] Field of Search ................................. 585/417, 419

[56] References Cited

U.S. PATENT DOCUMENTS

| | | | |
|---|---|---|---|
| 4,496,785 | 1/1985 | Miller et al. | 585/419 |
| 4,504,691 | 3/1985 | Hsia et al. | 585/533 |
| 4,704,494 | 11/1987 | Inui | 585/417 |
| 4,727,206 | 2/1988 | Clayson et al. | 585/417 |
| 4,761,511 | 8/1988 | Barlow | 585/417 |
| 4,766,265 | 8/1988 | Desmond et al. | 585/417 |
| 4,806,701 | 2/1989 | Shum | 585/419 |
| 4,808,763 | 2/1989 | Shum | 585/417 |

FOREIGN PATENT DOCUMENTS

| | | | |
|---|---|---|---|
| 2232487 | 10/1987 | Japan | 585/419 |
| 0730055 | 5/1955 | United Kingdom | 585/419 |

*Primary Examiner*—Patrick P. Garvin
*Assistant Examiner*—E. D. Irzinsia
*Attorney, Agent, or Firm*—Ekkehard Schoettle; William H. Magidson; Ralph C. Medhurst

[57] ABSTRACT

The present invention relates to a process for producing aromatic compounds from a hydrocarbon gas containing $C_3$ through $C_5$ paraffinic hydrocarbons under conversion conditions in the presence of a catalyst comprising a borosilicate molecular sieve, a platinum metal component and a gallium metal component.

14 Claims, No Drawings

PROCESS FOR UPGRADING LIGHT PARAFFINS

BACKGROUND OF THE INVENTION

The present invention is directed upgrading light paraffins such as propane, and butanes. Interest in upgrading these light paraffins has been growing due to recent and anticipated changes in refinery processing schemes which resulted and will result in a greater supply of such light paraffins. These changes include: the higher severity operation of the reforming process in order to maintain a high octane rating in the absence of or reduction of the lead content in gasoline; the lowering of reid vapor pressure (RVP) specifications; the increased use of oxygenates such as methyl tertiary butyl ether (MTBE) and ethanol resulting in the removal of butanes from the gasoline pool; the increased demand for jet fuel necessitating increased gas oil hydrocracking resulting in more light gas production, and the increase in operating temperatures in fluidized catalytic crackers resulting in more light gas production. Thus, there is great incentive to investigate means for converting these materials into more valuable liquids such as transportation fuels or chemical feedstocks.

The upgrading or conversion of light paraffinic gases and synthesis gas has previously been carried out in the presence of gallium-based or gallium-containing catalysts wherein such catalysts also contain various types of molecular sieves.

U.S. Pat. No. 4,543,347 (Heyward et al.) discloses a catalyst composition suitable for converting synthesis gas to hydrocarbons which is a mixture of zinc oxide and an oxide of at least one metal selected from gallium and iridium, an oxide of at least one additional metal collected from the elements of Groups IB, II through V, VIB and VIII including the lanthanides and actinides and a porous crystalline tectometallic silicate.

U.S. Pat. No. 4,490,569 (Chu et al.) discloses a process for converting propane to aromatics over a zinc-gallium zeolite This zeolite optionally may also contain palladium. More specifically, the catalyst composition used in the instant patent consists essentially of an aluminosilicate having gallium and zinc deposited thereon or an aluminosilicate in which cations have been exchanged with gallium and zinc ions wherein the aluminosilicate is selected from the group known as ZSM-5 type zeolites.

U.S. Pat. No. 4,585,641 (Barri et al.) discloses crystalline gallosilicates which may be impregnated, ion-exchanged, admixed, supported or bound for catalyzing a reaction such as alkylation, dealkylation, dehydrocyclodimerization, transalkylation, isomerization, dehydrogenation, hydrogenation, cracking, hydrocracking, cyclization, polymerization, conversion of carbon monoxide and hydrogen mixtures through hydrocarbons and dehydration reaction. The metal compounds which may be used for ion exchange or impregnation may be compounds of any one of the groups of metals belonging to Groups IB, IIB, IIIA, IVA, VA, VIB, VIIB and VIII according to the Periodic Table. Specifically, preferred compounds include copper, silver, zinc, aluminum, gallium, indium, vanadium, lead, antimony, bismuth, chromium, molybdenum, tungsten, manganese, iron, cobalt, nickel, ruthenium, rhodium, palladium, iridium, platinum, radium, thorium and the rare earth metals. Patentees describe their gallosilicate as "Gallo Theta-1" in contradistinction to an MFI-type gallosilicate which has a substantially different X-ray diffraction pattern.

U.S. Pat. No. 4,350,835 (Chester et al.) relates to a catalytic process for converting gaseous feedstocks containing ethane to liquid aromatics by contacting the feed in the absence of air or oxygen under conversion conditions with a crystalline zeolite catalyst having incorporated therein a minor amount of gallium thereby converting the ethane to aromatics. The gallium is present in the catalyst as gallium oxide or as gallium ions if cations in the aluminosilicate have been exchanged with gallium ions. The patent further discloses that the original alkali metal of the zeolite, when it has been synthesized in the alkali metal form, may be converted to the hydrogen form or be replaced by ion exchange with other suitable metal cations of Groups I through VIII of the Periodic Table, including nickel, copper, zinc, palladium, calcium or rare earth metals.

European Patent Specification 0 050 021 discloses a process for producing aromatic hydrocarbons from a hydrocarbon feedstock containing at least 70 wt. % $C_2$ with a catalyst composition comprising an aluminosilicate having gallium deposited thereon and/or an aluminosilicate in which cations have been exchanged with gallium ions, where the aluminosilicate has a silica to alumina molar ratio of at least 5:1.

European patent application 0 107 876 discloses a process for producing an aromatic hydrocarbon mixture from a feedstock containing more than 50 wt. % $C_2$ through $C_4$ paraffins. Specifically, the process is carried out in the presence of crystalline gallium-silicate having a $SiO_2/Ga_2O_3$ molar ratio of 25 to 250 and a $Y_2O_3/GaO_3$ molar ratio lower than 1 where Y can be aluminum, iron, cobalt or chromium. The disclosure also teaches a two-step silicate treatment comprising a coke deposition and a coke burn-off with an oxygen-containing gas.

European patent application 0 107 875 similarly discloses a process for producing an aromatic hydrocarbon mixture from a feedstock comprising more than 50 wt. % of $C_2$ through $C_4$ paraffins This process is carried out in the presence of a crystalline gallium-silicate, having a $SiO_2/Ga_2O_3$ molar ratio of 25 to 100 and a $Y_2O_2/Ga_2O_3$ molar ratio lower than 1 where Y can be aluminum, iron, cobalt or chromium.

Other patents that disclose processes for upgrading light paraffins using gallium-containing catalysts include:

U.S. Pat. No. 4,613,716 McNiff)
U.S. Pat. No. 4,766,264 (Bennett et al.)
U.S. Pat. No. 4,276,437 (Chu)
U.S. Pat. No. 4,629,818 (Burress)

Light paraffinic gases have also been upgraded to liquid aromatics in the presence of crystalline aluminosilicate zeolite catalysts having incorporated therein a minor amount of a metal selected from Groups VIII, IIB, and IB of the Periodic Table. For instance, U.S. Pat. No. 4,120,910 (Chu) discloses copper-zinc-HZSM-5, platinum-HZSM-5, copper-HZSM-5, and zinc-HZSM-5 catalysts suitable for upgrading a gaseous paraffinic hydrocarbon feed to aromatic compounds.

U.S. Pat. No. 4,704,494 (Inui) discloses a process for the conversion of low molecular paraffin hydrocarbons to aromatic hydrocarbons in the presence of metallosilicates wherein the metal is Al, Ga, Ti, Zr, Ge, La, Mn, Cr, Sc, V, Fe, W, Mo, or Ni.

International Application No. PCT/GB84/00109 (International Publication Number: WO84/03879) (Barlow) discloses an aromatization process utilizing a catalyst having a Group VIII metal in combination with a galloaluminosilicate.

It has now been discovered that $C_3$ through $C_5$ light paraffins can most effectively be upgraded by the catalytic process of the present invention minimizing methane and ethane production while simultaneously maximizing the production of benzene, toluene, and xylenes.

The process of the present invention involves the use of an AMS-1B crystalline borosilicate molecular sieve. This sieve is disclosed in U.S. Pat. Nos. 4,268,420 and 4,269,813 (both to Klotz) both of which are incorporated herein by reference. The '420 patent broadly discloses the use of the AMS-1B crystalline borosilicates for various hydrocarbon conversion processes and chemical adsorption. Some of the hydrocarbon conversion processes for which the borosilicates appear to have relatively useful catalytic properties are fluidized catalytic cracking; hydrocracking; the isomerization of normal paraffins and naphthenes; the reforming of naphthas and gasoline-boiling-range feedstocks; the isomerization of aromatics, especially the isomerization of alkylaromatics, such as xylenes; the disproportionation of aromatics, such as toluene, to form mixtures of other more valuable products including benzene, xylene, and other higher methyl-substituted benzenes; hydrotreating; alkylation; hydrodealkylation; hydrodesulfurization; and hydrodenitrogenation. They are particularly suitable for the isomerization of alkylaromatics, such as xylenes, and for the conversion of ethylbenzene. The AMS-1B borosilicates, in certain ion-exchanged forms, can be used to convert alcohols, such as methanol, to useful products, such as aromatics or olefins.

It should also be noted that hydrogen processing catalysts containing an AMS-1B borosilicate molecular sieve coupled with catalytic metal components are also known. For instance, U.S. Pat. No. 4,434,047 (Hensley, Jr. et al.) discloses a catalytic dewaxing hydrotreating process using a catalyst containing a shape-selective cracking component such as an AMS-1B borosilicate molecular sieve, and a hydrogenating component containing Cr, at least one other Group VIB metal and at least one Group VIII metal. U.S. Pat. No. 4,268,420 similarly discloses an AMS-1B crystalline borosilicate which can be used in intimate combination with a hydrogenating component, such as tungsten, vanadium, molybdenum, rhenium, nickel, cobalt, chromium, manganese, or a noble metal, such as platinum or palladium, or rare earth metals, where a hydrogenation-dehydrogenation function is to be performed.

U.S. Pat. No. 4,563,266 (Hopkins et al.) discloses an AMS-1B crystalline borosilicate molecular sieve combined with at least one Group VIII noble metal for use in a catalytic dewaxing process. U.S. Pat. No. 4,738,768 (Tait et al.) likewise discloses the use of an AMS-1B borosilicate in a hydrocarbon pour point reducing process.

U.S. Pat. No. 4,451,685 (Nevitt et al.) discloses a process to convert propylene to gasoline blending stock products. Specifically, $C_2$ through $C_3$ olefins are converted to a mixture of $C_4$ through $C_8$ aliphatics and $C_6$ through $C_9$ aromatics in the presence of hydrogen and a catalyst. The catalyst employed is a crystalline AMS-1B borosilicate that may be impregnated with catalytically active materials including the metals of Groups IB, IIA, IIIA, IIIB, IVB, VB, VIB, VIIB and VIII and rare earth elements.

U.S. Pat. No. 4,433,190 (Sikkenga et al.) discloses a process to convert substantially linear alkanes such as normal alkanes having two to twenty carbon atoms to dehydrogenated and isomerized products in the presence of hydrogen and an AMS-1B crystalline borosilicate-based catalyst composition. This catalyst contains a noble metal and may also contain an ion or molecule of a Group IB, IIIB, IVB, VB, VIB, VIIB or VIII metal or a rare earth element.

Finally, U.S. Pat. No. 4,766,265 (Desmond) teaches a process for the conversion of ethane to liquid aromatic compounds using a catalyst containing a gallium impregnated molecular sieve with both a rhenium component and a metal selected from the group consisting of nickel, palladium, platinum, rhodium and iridium. The molecular sieve can be an alumino-, gallo-, or borosilicate. The '265 process is directed to handling ethane rich feedstocks ranging from 100% ethane to a feedstock containing only minor amounts of ethane in a feedstock predominantly of hydrogen, methane and relatively minor amounts of $C_2$–$C_5$ olefins and $C_3$–$C_5$ paraffins.

In contrast to the '265 process, the process of the present invention is directed to the conversion of a hydrocarbon gas rich in $C_3$ through $C_5$ light paraffins, preferably a feedstock rich in either $C_3$ and/or $C_4$. Further, the process of the present invention does not require the presence of a rhenium metal component in the catalyst.

It has now been discovered that $C_3$ through $C_5$ paraffins can most effectively be upgraded by the catalytic process of the present invention minimizing methane and ethane production while simultaneously maximizing the production of benzene, toluene and xylenes.

SUMMARY OF THE INVENTION

Briefly stated, in a broad aspect, this invention relates to a process for producing aromatic compounds from a hydrocarbon gas rich in paraffinic hydrocarbons ranging from $C_3$ to $C_5$ under conversion conditions in the presence of a catalyst comprising a borosilicate molecular sieve, a platinum metal component and a gallium metal component.

DETAILED DESCRIPTION OF THE INVENTION

The present invention deals with the conversion of a hydrocarbon gas rich in paraffinic hydrocarbons ranging from $C_3$ to $C_5$ to aromatics. A particularly suitable feedstock for use in the present invention contains $C_3$ and/or through $C_4$ light paraffins. The feedstock suitable for use in the present invention preferably contains less than 10% ethane and most preferably a relatively minor amount of ethane such as less than 5%. Minor amounts of methane can also be present. In addition to the mentioned paraffins, the feedstock may contain other light gases such as propylene, butene, isobutene, butadiene, and paraffins and olefins with five or more carbon atoms per molecule. These feedstocks are generally available from several sources in a refinery as elucidated above.

The process of the invention provides for the direct conversion of the light paraffinic gases to valuable aromatic hydrocarbons such as benzene, toluene, and xylenes. These aromatics can be used as an additive component to increase the octane number of gasoline or as raw materials in the petrochemical industry.

The process of the invention selectively provides for a high yield of benzene, toluene, and xylenes in the $C_4+$ product fraction while minimizing the yield of light $C_1$ and $C_2$ gases and $C_9+$ aromatic compounds in the product fraction.

Broadly, the catalyst employed according to the process of the present invention comprises a borosilicate molecular sieve component, a platinum metal component and a gallium metal component.

The catalyst system which is useful in this invention comprises a borosilicate catalyst system based on a molecular sieve material identified as AMS-1B. Details as to the preparation of AMS-1B are described in U.S. Pat. No. 4,269,813. Such AMS-1B crystalline borosilicate generally can be characterized by the X-ray pattern listed in Table I and by the composition formula:

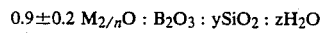

wherein M is at least one cation, n is the valence of the cation, y is between 4 and about 600 and z is between 0 and about 160.

TABLE I

| d-Spacing Å (1) | Assigned Strength (2) |
| --- | --- |
| 11.2 ± 0.2 | W-VS |
| 10.0 ± 0.2 | W-MS |
| 5.97 ± 0.07 | W-M |
| 3.82 ± 0.05 | VS |
| 3.70 ± 0.05 | MS |
| 3.62 ± 0.05 | M-MS |
| 2.97 ± 0.02 | W-M |
| 1.99 ± 0.02 | VW-M |

(1) Copper K alpha radiation
(2) VW = very weak; W = weak; M = medium; MS = medium strong; VS = very strong The AMS-1B borosilicate molecular sieve useful in this invention can be prepared by crystallizing an aqueous mixture, at a controlled pH, of sources for cations, an oxide of boron, an oxide of silicon, and an organic template compound.

Typically, the mole ratios of the various reactants can be varied to produce the crystalline borosilicates of this invention. Specifically, the mole ratios of the initial reactant concentrations are indicated below:

|  | Broad | Preferred | Most Preferred |
| --- | --- | --- | --- |
| $SiO_2/B_2O_3$ | 5-400 | 10-150 | 10-80 |
| $R_2O^+/[R_2O^+ + M_{2/n}O]$ | 0.1-1.0 | 0.2-0.97 | 0.3-0.97 |
| $OH^-/SiO_2$ | 0.01-11 | 0.1-2 | 0.1-1 |
| $H_2O$—$OH^-$ | 10-4000 | 10-500 | 10-500 | wherein R is an organic compound and M is at least one cation having a valence n, such as an alkali metal or an alkaline earth metal cation. By regulation of the quantity of boron (represented as $B_2O_3$) in the reaction mixture, it is possible to vary the $SiO_2/B_2O_3$ molar ratio in the final product.

More specifically, the material useful in the present invention is prepared by mixing a cation source compound, a boron oxide source, and an organic template compound in water (preferably distilled or deionized). The order of addition usually is not critical although a typical procedure is to dissolve sodium hydroxide and boric acid in water and then add the template compound. Generally, after adjusting the pH, the silicon oxide compound is added with intensive mixing such as that performed in a Waring Blender. After the pH is checked and adjusted, if necessary, the resulting slurry is transferred to a closed crystallization vessel for a suitable time. After crystallization, the resulting crystalline product can be filtered, washed with water, dried, and calcined.

During preparation, acidic conditions should be avoided. When alkali metal hydroxides are used, the values of the ratio of $OH^-/SiO_2$ shown above should furnish a pH of the system that broadly falls within the range of about 9 to about 13.5. Advantageously, the pH of the reaction system falls within the range of about 10.5 to about 11.5 and most preferably between about 10.8 and about 11.2.

Examples of oxides of silicon useful in this invention include silicic acid, sodium silicate, tetraalkyl silicates and Ludox, a stabilized polymer of silicic acid manufactured by E. I. du Pont de Nemours & Co. Typically, the oxide of boron source is boric acid although equivalent species can be used such as sodium borate and other boron-containing compounds.

Cations useful in formation of AMS-1B include alkali metal and alkaline earth metal cations such as sodium, potassium, lithium, calcium and magnesium. Ammonium cations may be used alone or in conjunction with such metal cations. Since basic conditions are required for crystallization of the molecular sieve of this invention, the source of such cation usually is a hydroxide such as sodium hydroxide. Alternatively, AMS-1B can be prepared directly in the hydrogen form by replacing such metal cation hydroxides with an organic base such as ethylenediamine.

Organic templates useful in preparing AMS-1B crystalline borosilicate include alkylammonium cations or precursors thereof such as tetraalkylammonium compounds. A useful organic template is tetra-n-propylammonium bromide. Diamines, such as hexamethylenediamine, can be used.

In a more detailed description of a typical preparation of this invention, suitable quantities of sodium hydroxide and boric acid ($H_3BO_3$) are dissolved in distilled or deionized water followed by addition of the organic template. The pH may be adjusted between about 11.0±0.2 using a compatible acid or base such as sodium bisulfate or sodium hydroxide. After sufficient quantities of silicic acid polymer (Ludox) are added with intensive mixing, preferably the pH is again checked and adjusted to a range of about 11.0±0.2. The resulting slurry is transferred to a closed crystallization vessel and reacted usually at a pressure at least the vapor pressure of water for a time sufficient to permit crystallization which usually is about 0.25 to about 20 days, typically is about one to about ten days and preferably is about five to about seven days, at a temperature ranging from about 100° to about 250° C., preferably about 125° to about 200° C. The crystallizing material can be stirred or agitated as in a rocker bomb. Preferably, the crystallization temperature is maintained below the decomposition temperature of the organic template compound. Especially preferred conditions are crystallizing at about 165° C. for about five to about seven days. Samples of material can be removed during crystallization to check the degree of crystallization and determine the optimum crystallization time.

The crystallization material formed can be separated and recovered by well-known means such as filtration with washing. This material can be mildly dried for anywhere from a few hours to a few days at varying temperatures, typically about 25°-200° C., to form a dry cake which can then be crushed to a powder or to small particles and extruded, pelletized, or made into forms suitable for its intended use. Typically, materials prepared after mild drying contain the organic template compound and water of hydration within the solid mass and a subsequent activation or calcination procedure is necessary, if it is desired to remove this material from the final product. Typically, mildly dried product is calcined at temperatures ranging from about 260° to about 850° C. and preferably about 525° to about 600° C. Extreme calcination temperatures or prolonged crystallization times may prove detrimental to the crystal structure or may totally destroy it. Generally there is no need to raise the calcination temperature beyond about 600° C. in order to remove organic material from the originally formed crystalline material. Typically, the molecular sieve material is dried in a forced draft oven at 165° C. for about 16 hours and is then calcined in air in a manner such that the temperature rise does not exceed 125° C. per hour until a temperature of about 540° C. is reached. Calcination at this temperature usually is continued for about 4 to 16 hours.

Although not required, it is preferred to employ the above-described borosilicate molecular sieve combined, dispersed or otherwise intimately admixed in a matrix of at least one non-molecular sieve, porous refractory inorganic oxide matrix component, as the use of such a matrix component facilitates the provision of the ultimate catalyst in a shape or form well suited for process use. Useful matrix components include alumina, silica, silica-alumina, zirconia, titania, etc., and various combinations thereof. The matrix components also can contain various adjuvants such as phosphorus oxides, boron oxides, and/or halogens such as fluorine or chlorine. Usefully, the molecular sieve-matrix dispersion contains about 1 to 99 wt. % of a sieve component, preferably 20 to about 90 wt. % and most preferably 30 to 80 wt. % of a sieve component based upon the sieve-matrix dispersion weight.

Methods for dispersing molecular sieve materials within a matrix component are well-known to persons skilled in the art and applicable with respect to the borosilicate molecular sieve materials employed according to the present invention. A method is to blend the molecular sieve component, preferably in finely-divided form, in a sol, hydrosol or hydrogel of an inorganic oxide, and then add a gelling medium such as ammonium hydroxide to the blend, with stirring, to produce a gel. The resulting gel can be dried, shaped if desired, and calcined. Drying preferably is conducted in air at a temperature of about 80° to about 350° F. (about 27° to about 177° C.) for a period of several seconds to several hours. Calcination preferably is conducted by heating in air at about 800° to about 1,200° F. (about 427° to about 649° C.) for a period of time ranging from about ½ to about 16 hours.

Another suitable method for preparing a dispersion of the molecular sieve component in a porous refractory oxide matrix component is to dry blend particles of each, preferably in finely-divided form, and then shape the dispersion if desired.

Alternatively, in another method, the sieve and a suitable matrix material like alpha-alumina monohydrate such as Conoco Catapal SB Alumina can be slurried with a small amount of a dilute weak acid such as acetic acid, dried at a suitable temperature under about 200° C., preferably about 100° to about 150° C. and then calcined at between about 350° and about 700° C., more preferably between about 400° to about 650° C.

Silica-supported catalyst compositions can be made by dry mixing the borosilicate sieve with a silica source such as Cab-O-Sil, adding water and stirring. The resulting solid is then dried below about 200° C. and finally calcined between about 350° C. and 700° C.

A catalytically active metal component present in the catalyst of the instant invention can be placed onto the borosilicate structure by ion exchange, impregnation, a combination thereof, or other suitable contact means. Before placing a catalytically active metal ion or compound on the borosilicate structure, the borosilicate may be in the hydrogen form which, typically, is produced by exchange one or more times with ammonium ion, typically using ammonium acetate, followed by drying and calcination as described above.

The metal components of the catalyst employed according to the present invention can be present in elemental form, as oxides, as nitrates, as chlorides or other inorganic salts, or as combinations thereof. While other Group VIII metals can be employed in the present invention, platinum is preferred because it is relatively inactive for hydrogenolysis which would result in undesirable increased yields of $C_1$ and $C_2$. Relative proportions of the sieve component, the platinum metal component and the gallium metal component are such that at least a catalytically-effective amount of each is present.

The platinum metal component content preferably ranges from about 0.01 to about 10 wt. %, calculated as a zero valent metal and being based on the total weight of the catalytic final composite, with about 0.01 to about 5 wt. % being more preferred, with a range of 0.05 to 1.0 wt. % being most preferred. Higher levels of platinum can be employed if desired, though the degree of improvement resulting therefrom typically is insufficient to justify the added cost of the metal.

The gallium metal component content preferably ranges from about 0.01 to about 10 wt. % calculated as the zero valent metal and based on the total weight of the final catalytic composite, a range of from 0.1 to 8 wt. % being more preferred and with a range of 0.5 to 5 wt. % being most preferred.

The platinum and gallium metal components of the catalyst employed according to this invention can be associated with the sieve component by impregnation of the sieve component, or the sieve component can be dispersed in a porous refractory inorganic oxide matrix, with one or more solutions of compounds of the platinum metal component and gallium metal component which compounds are convertible to oxides on calcination. It also is contemplated, however, to impregnate a porous refractory inorganic oxide matrix component with such solutions of the platinum metal component and gallium metal component and then blend the sieve component with the resulting impregnation product. Accordingly, the present invention contemplates the use of catalysts in which the platinum metal and gallium metal components are deposed on the sieve component, on a sieve-matrix component dispersion or on the matrix component of a sieve-matrix component.

The mechanics of impregnating the sieve component, matrix component or sieve-matrix component with solutions of compounds convertible to metal oxides on calcination are well-known to persons skilled in the art and generally involve forming solutions of appropriate compounds in suitable solvents, preferably water, and then contacting the sieve matrix component or sieve matrix dispersion with an amount or amounts of solution or solutions sufficient to deposit appropriate amounts of metal or metal salts onto the sieve or sieve matrix dispersion. Useful metal compounds convertible to oxides are well-known to persons skilled in the art and include various ammonium salts as well as metal acetates, nitrates, anhydrides, etc.

In another embodiment of the present invention the catalyst of the present invention also contains chloride. The addition of chloride to the catalyst serves to increase the conversion and selectivity of the process of the invention to aromatics. A convenient method of adding the chloride is to include a predetermined volume of a solution containing a predetermined concentration of hydrochloric acid in the impregnating solution used to incorporate the platinum metal component with the catalyst.

Alternatively, the chloride can also be added during the impregnation of the metal salt if the metal salt contains chloride, such as hydrogen hexachloroplatinate ($H_2PtCl_6 \cdot 6H_2O$) If the chloride content in the chloride-containing metal salt is not sufficiently high, additional chloride can be added by the addition of hydrochloric acid to the impregnating solution.

In the instant embodiment of the invention, the catalyst broadly contains 0.1 to 10 wt. % chloride, preferably 0.5 to 5 wt. % chloride and most preferably 0.5 to 1.5 wt. % chloride based on the final catalyst weight.

Also contemplated within the purview of the present invention, chloride can be incorporated into the catalyst by the addition of chloride-containing compounds to the feed stream such as carbon tetrachloride, hydrochloric acid, in amounts such that the final catalyst contains the above prescribed amount of chloride.

The above-described catalysts can be employed in any suitable form such as spheres, extrudates, pellets, or C-shaped or cloverleaf-shaped particles.

The process of the present invention is carried out under suitable operating conditions set out below in Table II under which the feed is contacted with the above-described catalyst. It is also contemplated that a portion of the unconverted effluent stream can be recycled to the feed after separation from the aromatic products.

TABLE II

| Conditions | Broad | Preferred | Most Preferred |
|---|---|---|---|
| Temperature, °F. | 700–1400 | 800–1200 | 850–1150 |
| Total Pressure, psig | 0–500 | 0–300 | 0–100 |
| WHSV, $h^{-1}$ | 0.1–100 | 0.1–40 | 0.1–20 |

The present invention is described in further detail in connection with the following examples, it being understood that the same are for purposes of illustration only and not limitation.

EXAMPLE 1

The present example demonstrates the process of the invention as it contrasts with two comparative processes.

The catalyst used in accordance with the present invention was prepared with a base composed of 40 wt. % AMS-1B borosilicate molecular sieve dispersed in 60 wt. % PHF gamma-alumina. This base was hot-exchanged with an aqueous ammonium acetate solution at 90°–100° C., then dried at about 250° F. followed by calcination at 900°–1000° F. This base was impregnated with an aqueous solution of gallium nitrate hydrate to result in a final catalyst having 1.0 wt. % Ga. The Ga-impregnated base was then dried at about 250° F. and calcined at 900°–1000° F. This Ga-containing base was then impregnated with an aqueous solution of tetraamineplatinum (II) nitrate to yield a final catalyst having 0.1 wt. % Pt. The Pt-impregnated-Ga-containing base was then dried at about 250° F. and then calcined at 900°–1000° F.

Two comparative catalysts, catalyst A and catalyst B were prepared in a similar manner as the catalyst of the invention except catalyst A did not contain any metals whereas catalyst B contained only gallium and no platinum. The gallium was present in catalyst B in the same amount as in the above-exemplified catalyst of the invention. The process of the invention and the comparative processes utilizing catalysts A and B were tested for propane conversion in a continuous-flow fixed-bed reactor under the following conditions:

Temperature = 994° F.
Total pressure = 50 psig
Catalyst weight = 1.5 g
Propane liquid rate = 24 ml/h
Nitrogen diluent rate = 100 cc(NTP)/min In each case the catalyst was pretreated in situ with nitrogen at about 1000° F. for 0.5 hours followed by a hydrogen treatment at about 1000° F. for 1 hour. The results are set out below in Table III where product selectivities and total conversion are shown in wt. %.

TABLE III

|  | Invention | Comparative A | Comparative B |
|---|---|---|---|
| Methane | 6.1 | 26.9 | 13.8 |
| Ethane + Ethylene | 29.4 | 68.6 | 41.1 |
| C4+ aliphatics | 22.9 | 4.5 | 15.7 |
| Benzene | 6.8 | 0 | 6.3 |
| Toluene | 18.2 | 0 | 15.1 |
| Xylenes | 13.4 | 0 | 8.0 |
| C9+ aromatics | 3.2 | 0 | 0 |
| Total conversion | 8.2 | 3.6 | 5.5 |
| Hours on stream | 5 | 3 | 2 |

The process of the invention clearly manifested the least methane, and ethane plus ethylene selectivity coupled with the highest selectivity for benzene, toluene, and xylenes.

What is claimed is:

1. A process for converting a gaseous hydrocarbon feed containing $C_3$ through $C_5$ paraffinic hydrocarbons to aromatic hydrocarbons which comprises contacting the feed under conversion conditions with a catalyst composition comprising a borosilicate molecular sieve, a platinum metal component and a gallium metal component.

2. The process of claim 1 wherein the gaseous feed comprises $C_3$ and $C_4$ paraffins.

3. The process of claim 2 wherein the gaseous feed comprises butane.

4. The process of claim 1 wherein the borosilicate molecular sieve is dispersed within a non-molecular sieve containing porous refractory inorganic oxide matrix component.

5. The process of claim 1 wherein the platinum metal component is present in an amount ranging from about 0.01 to about 10 wt. % calculated as the zero valent metal and based on the total weight of the composition.

6. The process of claim 1 wherein the gallium metal component is present in an amount ranging from about 0.01 to about 10 wt. % calculated as the zero valent metal and based on the total weight of the composition.

7. The process of claim 4 wherein the borosilicate molecular sieve is present in the dispersion such that the weight of the borosilicate ranges from about 20 to about 90 wt. % based on the weight of the borosilicate-refractory inorganic oxide dispersion.

8. The process of claim 4 wherein the borosilicate molecular sieve is present in the dispersion such that the weight of the borosilicate ranges from about 30 to 80 wt. % based on the weight of the borosilicate-refractory inorganic oxide dispersion.

9. The process of claim 4 wherein the refractory inorganic oxide component is selected from a group consisting of silica, silica-alumina, and alumina.

10. The process of claim 1 wherein the platinum metal component is present in an amount ranging from about 0.01 to about 5 wt. % calculated as the zero valent metal and based on the total weight of the composition.

11. The process of claim 1 wherein the gallium metal component is present in an amount ranging from about 0.1 to about 8 wt. % calculated as the zero valent metal and based on the total weight of the composition.

12. The process of claim 1 wherein the platinum metal component is present in an amount ranging from about 0.05 to about 1.0 wt. % and the gallium metal component is present in an amount ranging from about 0.5 to about 5 wt. % both calculated as the zero valent metal and based on the total weight of the final composition.

13. The process of claim 7 wherein the platinum metal component is present in an amount ranging from about 0.05 to about 1.0 wt. % and the gallium metal component is present in an amount ranging from about 0.5 to about 5 wt. % both calculated as the zero valent metal and based on the total weight of the final composition.

14. The process of claim 8 wherein the platinum metal component is present in an amount ranging from about 0.05 to about 1.0 wt. % and the gallium metal component is present in an amount ranging from about 0.5 to about 5 wt. % both calculated as the zero valent metal and based on the total weight of the final composition.

* * * * *